(12) United States Patent
Jia et al.

(10) Patent No.: US 6,592,372 B2
(45) Date of Patent: Jul. 15, 2003

(54) METHOD OF ETCHING AND PRIMING A TOOTH

(75) Inventors: Weitao Jia, Wallingford, CT (US); Bruce Alpert, Madison, CT (US); Martin L. Schulman, Orange, CT (US)

(73) Assignee: Jeneric/Pentron Incorporated, Wallingford, CT (US)

( * ) Notice: Subject to any disclaimer, the term of this patent is extended or adjusted under 35 U.S.C. 154(b) by 0 days.

(21) Appl. No.: 09/854,110

(22) Filed: May 11, 2001

(65) Prior Publication Data

US 2002/0119426 A1 Aug. 29, 2002

Related U.S. Application Data

(60) Provisional application No. 60/203,471, filed on May 11, 2000, and provisional application No. 60/244,232, filed on Oct. 30, 2000.

(51) Int. Cl.⁷ .................................................. A61C 5/00
(52) U.S. Cl. ........................................ 433/215; 523/118
(58) Field of Search ................................ 433/215, 216, 433/226; 523/115, 116, 118

(56) References Cited

U.S. PATENT DOCUMENTS

| | | | |
|---|---|---|---|
| 4,593,054 A | | 6/1986 | Asmussen et al. |
| 4,802,950 A | | 2/1989 | Croll |
| 5,061,183 A | | 10/1991 | Nicholson |
| 5,256,065 A | | 10/1993 | Nicholson |
| 5,525,648 A | | 6/1996 | Aasen et al. |
| 5,756,560 A | | 5/1998 | Antonucci et al. |
| 5,849,813 A | * | 12/1998 | Oxman .................... 433/217.1 |
| 5,935,535 A | * | 8/1999 | Mitra ......................... 401/118 |
| 5,954,996 A | | 9/1999 | Discko |
| 6,004,390 A | | 12/1999 | Pflug et al. |
| 6,147,137 A | | 11/2000 | Jia |

* cited by examiner

*Primary Examiner*—Kevin Shaver
*Assistant Examiner*—Melba Bumgarner
(74) *Attorney, Agent, or Firm*—Ann M. Knab

(57) ABSTRACT

A method for etching and treating a tooth surface prior to restoration, comprising a solution comprising of an —$SO_3$ terminated compound resin, such as an —$SO_3H$ compound resin, and an aldehyde desensitizing compound. In practice, the composition is applied to the tooth surface and not subsequently washed prior to application of an adhesive or other restorative material.

6 Claims, 3 Drawing Sheets

METHOD OF ETCHING AND PRIMING A TOOTH

This application claims the benefit of provisional application Serial Nos. 60/203,471, filed May 11, 2000, and 60/244,232, filed Oct. 30, 2000.

TECHNICAL FIELD

The present invention relates to methods for preparing the surface of a tooth prior to repair or restoration. In particular, the present invention relates to compositions and methods for simultaneously etching and priming the surface of a tooth prior to the application of dental adhesives and/or filling materials.

BRIEF DESCRIPTION OF THE RELATED ART

Methods and compositions for improving the adhesion of resins to hard tissue, i.e., dentin or enamel, is an ongoing goal in the dental arts. Improved adhesion leads to longer lasting restorations and reduced tooth sensitivity. Numerous methods for preparing teeth for the application of a dental restorative material (such as a sealant, filling material, cementation of indirect dental restorations or the like) have accordingly been developed, including acid etch and priming steps. Unfortunately, such steps have increased operating time and complexity.

Acid etchants are commonly thought to remove smear layers and demineralize the tooth surfaces so as to promote effective mechanical bonding of the restorative material. However, the use of an etchant has a disadvantage, in that it must be washed off after application, requiring the time-consuming procedure of application, washing and drying. A further disadvantage of etchants is the perception that use of strong etchants can increase dental sensitivity in some patients.

In addition to acid etch procedures, adhesive strength is also improved by use of a primer. Primers are generally surface-active compounds that exhibit both an affinity for dentin and adhesive resin systems and participate in the polymerization process, thereby promoting adhesion between the primarily hydrophilic dentin and the predominantly hydrophobic polymeric adhesives or monomers from which they are formed. Primers are applied to dentin in solution form, commonly used solvents including acetone, ethanol, water, and various mixed solvent systems. A widely used primer is N-phenylglycine (NPG), which, in addition to its surface-active properties, also functions as a co-initiator or activator during interfacial polymerization. While effective for promoting bonding, primers are often applied using an additional step.

There accordingly remains a need in the art for improved compositions which improve adhesion, which do not increase tooth sensitivity, and yet which can be applied in a fewer number of steps.

SUMMARY OF THE INVENTION

The above-described drawbacks and disadvantages are alleviated by a self-etching primer composition comprising an olefinically unsaturated monomer having a terminal—$SO_3H$ functionality, selected from the group consisting of 2-acrylamido-2-methyl-propanesulfonic acid (AMPS), its esters, salts, and combinations thereof, 2-sulfoethyl methacrylate (SEM), its esters, salts, and combinations thereof, and 3-sulfopropyl methacrylate (SPM), its esters, salts, and combinations comprising at least one of the foregoing monomers. The monomer is present in quantities effective to provide etching and priming, generally in the range from about 0.1 to about 50 weight percent of the total composition. In a particularly advantageous feature, the composition will increase the adhesiveness of the tooth structure without the need for washing the composition from the tooth surface. This composition can accordingly be provided as a single component material for ease of application and storage. The composition further includes a desensitizing agent, in the form of an aldehyde having from 2 to about 20 carbon atoms, preferably glutaraldehyde, in an amount effective to decrease dental sensitivity. Metallic ion salts such as potassium nitrate or calcium chloride can also be added. Fluoride or a fluoride source may also be added to the composition.

In accordance with the method of use, the above-described composition is physically contacted with the tooth structure, and then at least partially dried prior to application of an adhesive or other restorative composition. No intermediate washing step or second primer application step is required.

BRIEF DESCRIPTION OF THE DRAWINGS

Features of the present invention are disclosed in the accompanying drawings, wherein similar reference characters denote similar elements throughout the several views, and wherein.

DETAILED DESCRIPTION OF THE PREFERRED EMBODIMENTS

Figure 1:
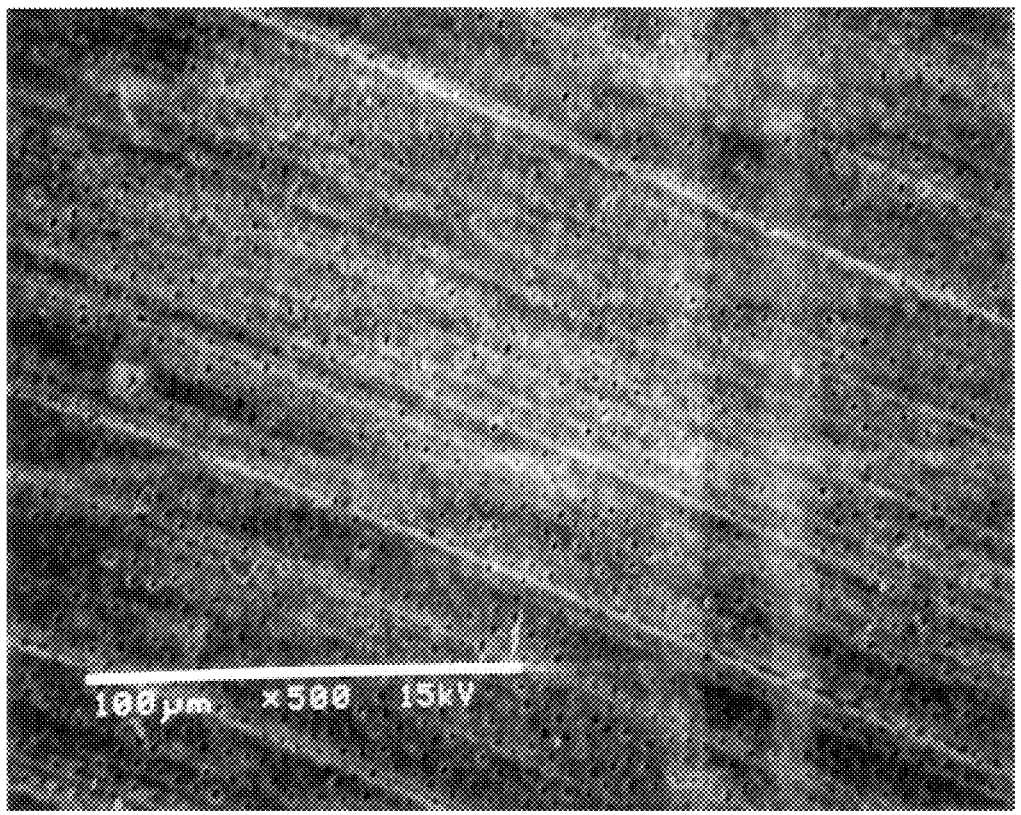
FIG. 1 is a micrograph showing exposed dentin surface after mechanical preparation.

The inventors hereof have unexpectedly discovered that monomers having both olefinic unsaturation and terminal —$SO_3$ groups, such as an —$SO_3H$ group, are effective to simultaneously etch and prime a tooth to receive a dental restoration. Examples of such compounds include 2-acrylamido-2-methyl-propanesulfonic acid (AMPS) and its derivatives, 2-sulfoethyl methacrylate (SEM) and its derivatives, and 3-sulfopropyl methacrylate (SPM) and its derivatives. Examples of derivatives include sulfonic acid salts of AMPS, SEM and SPM, and hydrolytically active esters of AMPS, SEM, and SPM. AMPS compounds are available from Lubrizol Corporation, Wickliffe, Ohio. SEM and SPM compounds are available from Polyscience, Inc., Pa.

A self-etching, priming composition in accordance with the present invention accordingly comprises a solution of a one or more of AMPS, SEM, SPM, and/or their derivatives. Suitable salt countering include without limitation alkali and alkaline earth metals. Suitable ester moieties include without limitation lower alkyl groups, for example methyl, ethyl, propyl, isopropyl, and the like, as well as aromatic groups such as benzyl.

Preferably, the —$SO_3$ terminated monomers are present in the solution in amounts from about 0.1 to about 50 weight percent, more preferably about 0.5 to about 20 weight percent, and most preferably from about 1 to about 10 weight percent of the total composition. The particular amounts are selected to provide effective etching and priming (enhanced adhesion).

The etchant/primer composition may further include an aldehyde in an amount effective to decrease sensitivity at the site of the dental restoration. Suitable aldehydes include aliphatic aldehydes having from 2 to about 20, preferably from 2 to about 10, and most preferably from 2 to about 6 carbon atoms. Aromatic and heteroaromatic aldehydes having from 6 to about 20 carbons may also be used. Dialdehydes are also within the scope of the invention. Exemplary aldehydes include but are not limited to acetic aldehyde, propionaldehyde, glyoxal, benzaldehyde, vanilline, salicylic aldehyde, o-phthalic aldehyde, anisaldehyde, furfural, and the like. Preferably, the desensitizing agent is glutaraldehyde.

When present, effective quantities of aldehyde are readily determined by one of ordinary skill in the art. In general, effective quantities comprise from about 0.1 to about 20% by weight, preferably from about 0.2 to about 10% by weight, and most preferably from about 0.5 to about 3% by weight of the total composition.

The etchant/primer adhesive composition may further include an optional fluoride source. Suitable fluoride sources which are compatible with AMPS and AMPS derivatives, SPM and SPM derivatives, and SEM and SEM derivatives include, for example, sodium fluoride, stannous fluoride, sodium monofluorophosphate, calcium fluorophosphate, and the like. When present, fluoride-releasing compounds are used in quantifies of up to about 2% by weight of the total composition.

The etchant/primer adhesive composition may further comprise additional, optional components for enhancing the priming, cleaning or conditioning effect of the composition. Such components include chemicals containing polymerizable double bonds such as those of methacrylic acid, ester, or similar groups; additional acids with good or limited solubility in water; surfactants; and dyes such as methylene blue, and the like. More specifically, examples of useful priming components include 2-hydroxyethylmethacrylate, glyceryl methacrylate, hydroxypropylmethacrylates, itaconic acid, ethyleneglycolmethacrylate, maleic acid 2-(methacryloyloxy)ethyl phosphate, and the like. These optional components are generally present in amounts in the range of up to about 50 weight percent.

The etchant/primer compositions further include a solvent. Such a solvent system includes water and/or a polar solvent that is partially or totally soluble in water. For dental applications, a suitable solvent system is one that completely wets and diffuses into the conditioned surface of enamel, and particularly dentin, in a clinically acceptable period of time (on the order of about 15 to about 180 seconds). Preferred organic solvents include low molecular weight ketones, such as acetone and methyl ethyl ketone, which are readily soluble in water over a wide concentration range, or a low molecular weight alcohol, such as ethanol or propanol. Other solvents include polar aprotic liquids such as dimethylformamide, dimethylacetamide and dimethylsulfoxide. Water, ethanol, acetone, or a mixed solvent system of water and acetone are preferred. In such a solvent system, the amount, by volume, of acetone may range from about 5 to about 50% acetone, with the remainder being water.

The solvent serves the purpose of assuring that the etchant/primer compound contacts all exposed dentin surfaces so that the etchant/primer compound can function successfully. Thus, the solvent system must appropriately reduce the viscosity of the etchant/primer compound as well as provide a suitable surface tension such that the composition may penetrate the smallest cracks, fissures or pores in the dentin surface to assure suitable contact of the polymerized adhesive component with the dentin. In some instances, to provide the appropriate surface tension, a surfactant may be employed. In most instances, as when the etchant/primer compound is combined with an adhesive monomer system, it is preferred that the solvent system used to dissolve the etchant/primer compound also be miscible with the solvent system employed to dissolve the adhesive monomer system and/or be capable of dissolving the adhesive monomer system itself.

The amount of solvent used is 100 weight percent less the total amount of other components, preferably 50 to 99 weight percent, more preferably 60 to 99 weight percent of the total composition. Distilled or deionized water is preferred, as it does not contain impurities potentially harmful to the adhesive properties of the solution. When volatile solvents such as ethanol or acetone are used in the composition, the amount of water may be decreased to as low as 2 percent.

The etchant/primer adhesive composition may be applied directly to the prepared tooth surface. The composition may be dispensed from a conventional push syringe or squeeze bottle, or applied with a brush. After a specified time ranging from 5 to 120 seconds, preferably 10 to 60 seconds, the tooth surface is lightly dried. Washing is not required. After applying the tooth surface treatment composition, a polymerizable dental adhesive system may be applied, dried, and optionally cured, followed by application and curing of a dental restorative material. The dental adhesive bonds to the tooth without the need for the tooth to be washed. Alternatively, the dental adhesive system may be included in the etchant/primer adhesive composition, combining the application of the etchant/primer and the application of the dental adhesive into a single step.

Suitable dental adhesives and restoratives are those conventional in the art. The term 'dental adhesive' and the like as used herein can apply to a wide range of materials that can effect a bond to both conditioned enamel and dentin. At a minimum, the dental adhesive contains a polymerizable resin component or components necessary to effect the initiation and acceleration of polymerization by visible or actinic light or by chemical means, and a polymerizable monomer or monomers containing anionic functionality such as a phosphate or carboxylic (COOH) acid function. Examples of monomers include triethylene glycol dimethacrylate (hereinafter TEGDMA), 2-hydroxyethylmethacrylate (hereinafter HEMA), 2,2-bis [p-(2'-hydroxy-3'-methacryloxypropoxy)phenyl]propane (hereinafter Bis-GMA), polyurethane dimethacrylates (hereinafter PUDMA), trimethylolpropane trimethacrylate (hereinafter TMPTMA), and the like. This dental adhesive may be in the form of a self-priming adhesive that further contains a volatile solvent such as acetone, ethanol, and mixtures thereof. Water may also be used as a solvent. The dental adhesive may comprise a one-component material, or may alternatively have two components. The second component of the dental adhesive may contain initiators and/or accelerators, to facilitate chemical curing alone or combined with curing upon exposure to actinic light to provide a dual-cure mode of polymerization. Examples of substances that facilitate self-curing of dental adhesives include for example, BPO, DHEPT, and aromatic sulfinic acid salts. One useful dental adhesive includes Bond One™ (available from Jeneric/Pentron, Inc.). Preferred dental adhesives are cured by exposure to light, preferably visible light.

Useful dental restorative materials or cements include amalgam and non-amalgam dental restoratives. Examples of useful non-amalgam materials include compomer restorative, composite resin restorative, glass ionomer-resin restorative, glass ionomer-resin luting cement, resin cement and resin dental sealant.

The composition, when applied to a tooth, enhances the adhesiveness of the tooth without the need for washing or a second application step. The multi-step bonding protocols typical of current commercial adhesive systems generally tend to be a source of material waste and unreasonable technique sensitivity. The present etchant/primer adhesive compositions not only reduce the number of steps normally involved in preparing a substrate surface and applying the adhesive monomer system (from 3 or 4 steps to 1 or 2 steps), but less waste and improved restorative or sealant results are obtained.

Furthermore, although conventional aggressive etchants are effective in cleaning the surface of dentin for improved wetting by and diffusion of the components of the adhesive system, they can also weaken the underlying sound dentin by excessive demineralization and disruption of collagen fibrils. These types of etchants typically require an aqueous rinse step to remove residual acid and soluble by-products. Also, the depth of demineralized, altered dentin resulting from the use of aggressive etchants may exceed the depth to which an adhesive resin can penetrate the dentin, resulting in a weakened, partially reinforced hybrid dentin zone, and thereby become vulnerable to failure. In contrast, the present composition is milder and may be used as single step etchant and primer compositions without subsequent rinsing since they are also effective in the presence of water and/or aqueous solvents. Accordingly, while an aqueous rinse step, such as the type used with multi-step systems to remove residual acid and soluble by-products, may be used, it is unnecessary to employ such a rinse step.

Figure 2:
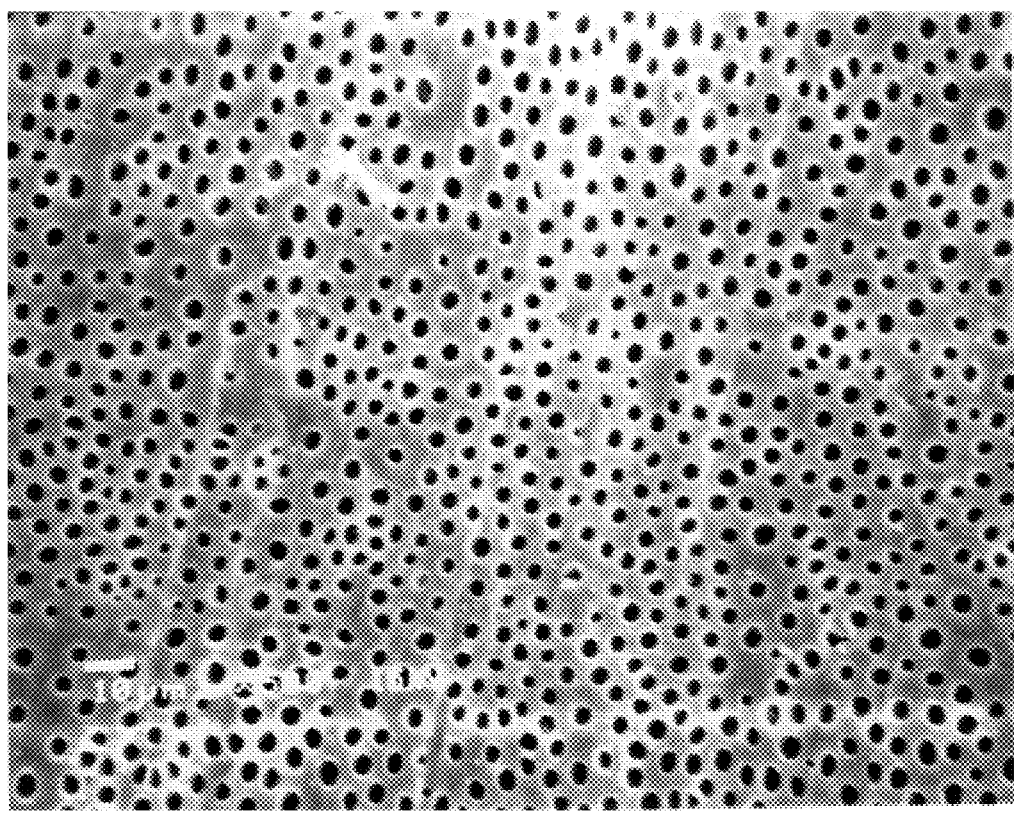
FIG. 2 is a micrograph showing dentin surface that has been etched with 37% $H_3PO_4$.
Figure 3:
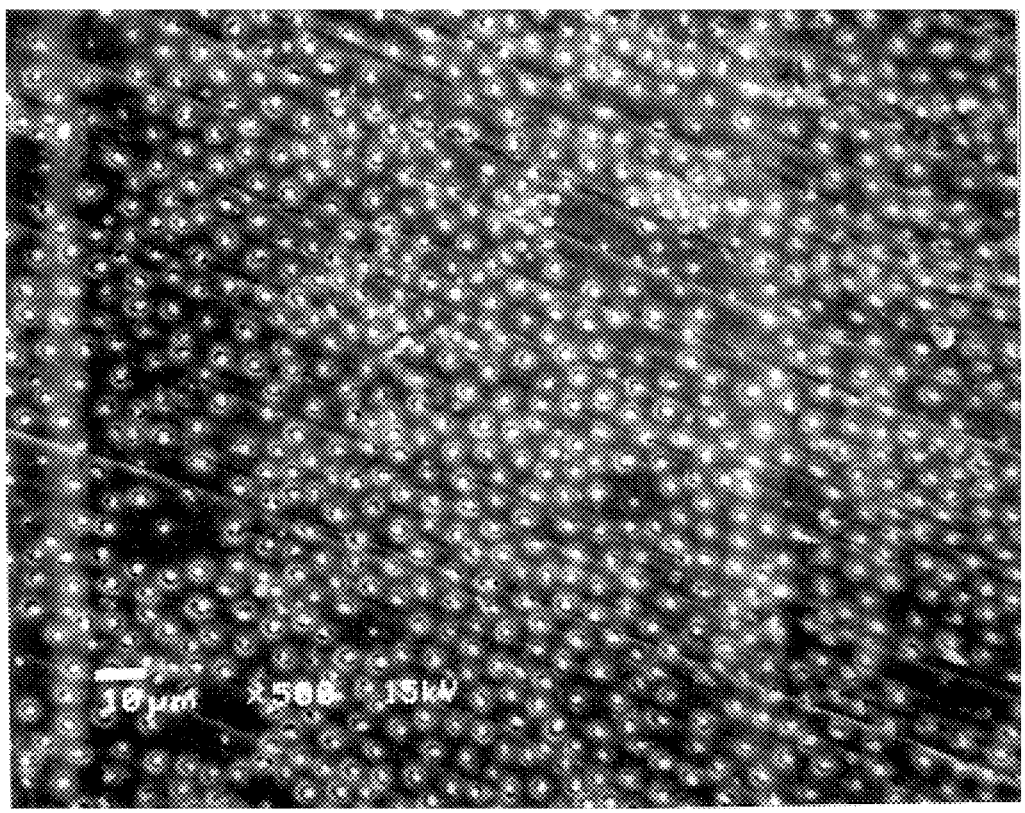
FIG. 3 is a micrograph showing dentin surface that has been etched with a primer in accordance with the invention.

Another advantage of the mildness of the present compositions is that sensitivity for the patient at the site of the restoration is reduced. Such sensitivity is reduced even further where an effective aldehyde (such as glutaraldehyde) is used. FIGS. 1 through 3 illustrate the differences in the dentin surface with respect to surface manipulation. FIG. 1 shows exposed dentin after mechanical abrasion. The surface was polished with Carbimet™ sandpaper grit 600 on a Handimet II Roll Grinder (Bueuhler Ltd., IL). The dentin tubes are opened, but minerals are intact around the tubes.

FIG. 2 shows dentin surface that has been mechanically abraded and polished as in FIG. 1 followed by application of a conventional phosphoric acid etchant, 37% $H_3PO_4$ etching gel (Jeneric/Pentron, Inc. CT) for 20 seconds. The surface is then rinsed with water and dried. The dentin tubes are broadly exposed because of the demineralization effect of the etching.

FIG. 3 shows dentin surface that has been treated with a self-etch primer composition of the invention containing 1% glutaraldehyde. After 30 seconds of treatment, the surface is dried without any rinsing. The dentin tubes are filled and the communication passes are blocked. Accordingly, the dentin surface is primed for application of a bonding agent, but is prevented from being oversensitive to the application of the dental restoration.

The following non-limiting examples illustrate the invention.

EXAMPLES

Etchant solutions of the invention comprising an aqueous solution of 2.2% AMPS resin and 1% glutaraldehyde were applied to the tooth surface for twenty seconds and gently air-dried for two seconds. Bonding agents were applied using the same procedure as that in U.S. Pat. No. 6,147,137, which is hereby incorporated by reference. Comparative examples were conducted using 37% $H_3PO_4$ gel, which was applied to the tooth surface for twenty seconds, and thereafter flushed with copious amounts of water for 10 seconds. The surfaces were gently air dried and the bonding agents were applied. Table 1 below sets forth the examples. As shown, the self-etching compositions of the invention show the same or better bonding results, but using less steps in the application of the etchant to the tooth surface.

TABLE 1

| Adhesive Brand (Lot Number) | Bonding to Dentin (MPa) Self-Etch* | Comparative Examples 37% $H_3PO_4$ gel | Bonding to Enamel (MPa) Self-Etch* | Comparative Examples 37% $H_3PO_4$ gel |
|---|---|---|---|---|
| Bond One (071200) | 21.6 (3.1) | 22.0 (4.0) | 23.4 (2.3) | 24.6 (3.5) |
| Excite (C08332) | 19.5 (7.2) | 18.9 (4.1) | | |
| Prime&Bond NT (000605) | 15.5 (5.3) | 17.1 (3.5) | | |
| One Step (00006939) | 25.2 (4.0) | 24.3 (4.8) | 22.1 (1.8) | 25.8 (5.1) |
| Single Bond (OEM) | 20.1 (6.3) | 18.8 (4.1) | 12.5 (2.7) | 14.7 (3.8) |
| OptiBond Solo (006504) | 20.0 (2.3) | 22.2 (4.2) | | |

*Aqueous solution of 2.2% AMPS resin and 1% glutaraldehyde

The foregoing description illustrates preferred embodiments of the invention. However, concepts employed may, based upon such description, be employed in other embodiments without departing from the scope of the invention. Accordingly, the following claims are intended to recite the invention broadly, as well as in the specific forms herein.

What is claimed is:

1. A method of etching and treating a tooth to increase adhesiveness, comprising:

applying an etchant and treatment composition comprising about 0.1 to about 50 weight percent of an olefinically unsaturated, —$SO_3$ terminated monomer selected from the group consisting of 2-acrylamido-2 methyl-propanesulfonic acid, derivatives of 2-acrylamido-2-methyl-propanesulfonic acid, 2-sulfoethyl methacrylate, derivatives of 2-sulfoethyl methacrylate, 3-sulfopropyl methacrylate, derivatives of 3-sulfopropyl methacrylate, and a mixture comprising at least one of the foregoing monomers;

and further comprising about 0.1 to about 20% by weight, of a desensitizing aldehyde, such that when the composition is applied to the tooth surface, the adhesiveness of the tooth surface is increased; and applying an adhesive composition to the surface without applying a separate primer composition.

2. A method of etching and treating a tooth to increase adhesiveness as set forth in claim 1, wherein the etchant and treatment composition further comprises one or more of hydroxyethylmethacrylate, itaconic acid, maleic acid, ethyltriglycol methacrylate, or 2-(methacryloyloxy)ethyl phosphate.

3. A method of etching and treating a tooth to increase adhesiveness as set forth in claim 1, wherein the olefinically unsaturated, —$SO_3$ terminated monomer is present in an amount from about 0.5 to about 20 percent by weight; wherein the desensitizing aldehyde is present in an amount from about 0.2 to about 10 percent by weight; and wherein water is present in an amount from about 70 to about 99 percent by weight.

4. A method of etching and treating a tooth to increase adhesiveness as set forth in claim 1, wherein the etchant and treatment composition further comprises from 0 to about 2 percent by weight of a fluoride component.

5. A method of etching and treating a tooth to increase adhesiveness as set forth in claim 1, wherein the aldehyde is glutaraldehyde.

6. A method of etching and treating a tooth to increase adhesiveness as set forth in claim 1, wherein the olefinically unsaturated, —$SO_3$ terminated monomer is present in an amount from about 1 to about 10 percent by weight; wherein the desensitizing aldehyde is present in an amount from about 0.5 to about 3 percent by weight; and wherein water is present in an amount from about 87 to about 98.5 percent by weight.

* * * * *